(12) United States Patent
Kovatchev et al.

(10) Patent No.: US 11,567,062 B2
(45) Date of Patent: Jan. 31, 2023

(54) SYSTEM AND METHOD FOR TRACKING CHANGES IN AVERAGE GLYCEMIA IN DIABETICS

(71) Applicant: University of Virginia Patent Foundation, Charlottesville, VA (US)

(72) Inventors: Boris P. Kovatchev, Charlottesville, VA (US); Marc D. Breton, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 572 days.

(21) Appl. No.: 15/580,915

(22) PCT Filed: Jun. 8, 2016

(86) PCT No.: PCT/US2016/036481
§ 371 (c)(1),
(2) Date: Dec. 8, 2017

(87) PCT Pub. No.: WO2016/200970
PCT Pub. Date: Dec. 5, 2016

(65) Prior Publication Data
US 2018/0313815 A1 Nov. 1, 2018

Related U.S. Application Data

(60) Provisional application No. 62/172,522, filed on Jun. 8, 2015.

(51) Int. Cl.
*G16H 50/20* (2018.01)
*G16H 10/40* (2018.01)
(Continued)

(52) U.S. Cl.
CPC .......... *G01N 33/49* (2013.01); *A61B 5/4866* (2013.01); *G16H 10/40* (2018.01); *G16H 20/17* (2018.01);
(Continued)

(58) Field of Classification Search
CPC .. A61B 5/14532; A61B 5/4866; G01N 33/49; G06F 19/3468; G16H 20/17; G16H 50/20; G16H 40/67
See application file for complete search history.

(56) References Cited

U.S. PATENT DOCUMENTS

2009/0171589 A1  7/2009  Kovatchev
2010/0280489 A1  11/2010  Yodfat et al.
(Continued)

FOREIGN PATENT DOCUMENTS

| WO | WO-2010094904 A1 * | 8/2010 | ............ G06F 19/00 |
| WO | WO-2014116701 A2 * | 7/2014 | ......... A61B 5/14532 |
| WO | 2016200970 A1 | 12/2016 | |

OTHER PUBLICATIONS

Nathan DM, Kuenen J, Borg R, Zheng H, Schoenfeld D, Heine RJ; A1c-Derived Average Glucose Study Group. Translating the A1C assay into estimated average glucose values. Diabetes Care. Aug. 2008;31(8):1473-8. doi: 10.2337/dc08-0545. Epub Jun. 7, 2008. Erratum in: Diabetes Care. Jan. 2009;32(1):207. PMID: 18540046; PMCID.*

(Continued)

*Primary Examiner* — Jay M. Patel
(74) *Attorney, Agent, or Firm* — Potomac Law Group, PLLC; Vincent M DeLuca; Brian H. Buck

(57) ABSTRACT

A computer-implemented method for providing a real-time estimate of glycosylated hemoglobin (HbA1c) of a patient from a self-monitoring blood glucose (SMBG) measurement, and tracking changes in average glycemia of said (Continued)

patient over time is disclosed. The method includes the steps of; a computer computing a surrogate fasting measurement based on SMBG data received from the patient; a computer computing a glycation value using the said surrogate fasting measurement in a predetermined glycation equation; a computer outputting said glycation value as an initial estimate of HbA1c upon initialization of tracking of said patient's average glycemia; a computer updating said glycation value by using an updated SMBG value in said predetermined glycation equation, said updated SMBG value being based on a subsequent computed surrogate fasting measurement; and a computer computing an updated estimate of HbA1c using said initial estimate of HbA1c and said updated glycation value in a predetermined HbA1c estimation equation.

30 Claims, 6 Drawing Sheets

(51) Int. Cl.
G16H 40/67 (2018.01)
G16H 40/40 (2018.01)
G01N 33/49 (2006.01)
G16H 20/17 (2018.01)
A61B 5/00 (2006.01)
A61B 5/145 (2006.01)

(52) U.S. Cl.
CPC ............ *G16H 40/40* (2018.01); *G16H 40/67* (2018.01); *G16H 50/20* (2018.01); *A61B 5/14532* (2013.01)

(56) References Cited

U.S. PATENT DOCUMENTS

| | | | | |
|---|---|---|---|---|
| 2010/0330598 | A1* | 12/2010 | Thukral | G16H 20/60 435/14 |
| 2011/0174638 | A1 | 7/2011 | Katsuki | |
| 2012/0095318 | A1 | 4/2012 | Galley et al. | |
| 2016/0004813 | A1* | 1/2016 | Kovatchev | G16B 5/00 702/19 |
| 2017/0067846 | A1* | 3/2017 | Schaible | A61B 5/4839 |
| 2017/0311897 | A1* | 11/2017 | Faccioli | A61B 5/7203 |
| 2018/0313815 | A1 | 11/2018 | Kovatchev et al. | |

OTHER PUBLICATIONS

Kovatchev et al., "Accuracy and Robustness of Dynamical Tracking of Average Glycemia (A1c) to Provide Real-Time Estimation of Hemoglobin A1c Using Routine Self-Monitored Blood Glucose Data," Diabetes Technology & Therapeutics, vol. 16, No. 5, Apr. 23, 2014.

* cited by examiner

SYSTEM AND METHOD FOR TRACKING CHANGES IN AVERAGE GLYCEMIA IN DIABETICS

CROSS REFERENCE TO RELATED APPLICATIONS

This application claims priority to U.S. Provisional Application Ser. No. 62/172,522, filed Jun. 8, 2015, and is related to International Application No. PCT/US2014/017754, filed Feb. 21, 2014, (the national stage of which was entered as U.S. application Ser. No. 14/769,638) which claims priority under 35 U.S.C. § 119(c) from U.S. Provisional Application Ser. No. 61/767,451, filed Feb. 21, 2013, entitled "Tracking Changes in Average Glycemia in Diabetics," the disclosures of which are hereby incorporated by reference herein in their entirety.

BACKGROUND

An approach to real-time estimation of $HbA_{1c}$ (hemoglobin A1c or glycated hemoglobin) from infrequent self-monitoring (SMBG) data was previously disclosed and incorporated herein by reference. The method introduced was designed to track changes in average glycemia and was based on a conceptually new approach to the retrieval of SMBG using a mathematical model to estimate HbA1c as the measurable aggregated effect of the action of an underlying dynamical system which translates ambient blood glucose (BG) levels into HbA1c values through hemoglobin glycation. This model-based approach was adopted because, while it is generally true that HbA1c is roughly proportional to the average BG of a person over the past 2-3 months and a number of linear and nonlinear formulas have been used to describe this relationship, it is also established that average BG estimated from HbA1c using a linear formula and average BG estimated from SMBG are discordant measures of glycemic control. The discrepancies have been quantified by the hemoglobin glycation index (HGI, equal to observed HbA1c-predicted HbA1c), where the prediction is a linear regression formula based on average BG derived from 7-point daily profiles collected quarterly, or on average fasting BG. Because the regression coefficients were study specific, derived from DCCT data in the case of 7-point profiles or from ACCORD study data in the case of fasting BG, the calculation of the HGI was also study-specific. Nevertheless, it was determined that DCCT patients in the high-HGI group (those with HbA1c higher than the estimate provided by linear regression) had 3 times greater risk of retinopathy and 6 times greater risk of nephropathy compared with the low-HGI group. Similarly, the reanalysis of the ACCORD study data determined that higher total mortality in intensively treated patients was confined to the high-HGI subgroup, and high HGI was associated with a greater risk for hypoglycemia in the standard and intensive treatment groups. Thus, these studies have confirmed the clinical significance of the biological variation in HbA1c that is not explained by linear models using SMBG data. It was further concluded that nonlinear dynamics methods should be employed to approximate HbA1c values instead of proportions based on average BG.

A dynamical tracking algorithm was previously introduced and incorporated herein by reference—a new two-step procedure that computes real-time estimates of HbA1c (eA1c) from fasting glucose readings, which are updated with any new incoming fasting SMBG data point. The eA1c is first initialized and then calibrated periodically with 7-point daily SMBG profiles taken approximately every month. The eA1c algorithm was developed using training data comprised of daily fasting SMBG readings and monthly 7-point daily profiles collected by patients with Type 2 diabetes. Then all model parameters were fixed and the algorithm was applied without further modification to independent test data, also collected in patients with Type 2 diabetes. The mean absolute relative difference (MARD)—the metric that is typically used to assess accuracy of any direct measurement or other assessment of unknown analyte—was <7%. Achieving MARD below 7% signified that the method was capable of providing accurate and precise tracking of changes in average glycemia over time. Specifically, the eA1c algorithm tracks average glycemia from SMBG data and then derives eA1c values that could be available daily. The key feature of this approach is that it is capable of working with infrequent SMBG data typical for type 2 diabetes, e.g. fasting readings on most days and occasional (monthly) 7-point SMBG profiles. Thus, the eA1c algorithm differed from all previously introduced techniques by its use of an underlying model that "filled in" the gaps between sparse SMBG values, thereby allowing continuous tracing of average glycemia.

SUMMARY

The same method is described herein but without any parameter alteration. Specifically, three new steps are taken:
(1) Reconstruct 7-point daily profiles from non-structured episodic SMBG data; thus eliminating the need for collecting special profiles, provided that sufficient SMBG readings are available;
(2) Validate the dynamical tracking eA1c algorithm in Type 1 diabetes;
(3) Correlate the results from the eA1c algorithm with the HGI, as previously defined, to gauge whether eA1c accounts for at least some of the biological variation causing discrepancies between HbA1c and its linear estimates from SMBG data.

BACKGROUND

Previously the eA1c has been introduced—a new approach to real-time tracking of average glycemia and estimation of HbA1c from infrequent self-monitoring (SMBG) data, which was developed and tested in Type 2 Diabetes. In the present disclosure, eA1c is tested in Type 1 diabetes and its relationship to the hemoglobin glycation index (HGI), an established predictor of complications and treatment effect, is assessed.

Methods:

Reanalysis of previously published 12-month data from 120 patients with Type 1 diabetes, age 39.15(14.35) years; 51/69 males/females; baseline HbA1c=7.99%(1.48), duration of diabetes 20.28(12.92) years; number SMBG/day=4.69(1.84). Surrogate fasting BG and 7-point daily profiles were derived from these unstructured SMBG data and the previously reported eA1c method was applied without any changes. Following the literature, we calculated HGI=HbA1c−(0.009*Fasting BG+6.8).

Results:

The correlation of eA1c with reference HbA1c was r=0.75 and its deviation from reference was MARD=7.98%; 95% of all eA1c values fell within ±20% from reference. The HGI was well approximated by a linear combination of the eA1c calibration factors: HGI=0.007552*$\theta_1$+

0.007645*θ₂−3.154 (p<0.0001); 73% of low- vs. moderate-high HGIs were correctly classified by the same factors as well.

CONCLUSIONS

The eA1c procedure developed in Type 2 diabetes to track in real time changes in average glycemia and present the results in HbA1c-equivalent units, has now been validated in Type 1 diabetes. The eA1c calibration factors are highly predictive of the HGI; thereby explaining partially the biological variation causing discrepancies between HbA1c and its linear estimates from SMBG data.

DETAILED DESCRIPTION

Methods

Figure 1:
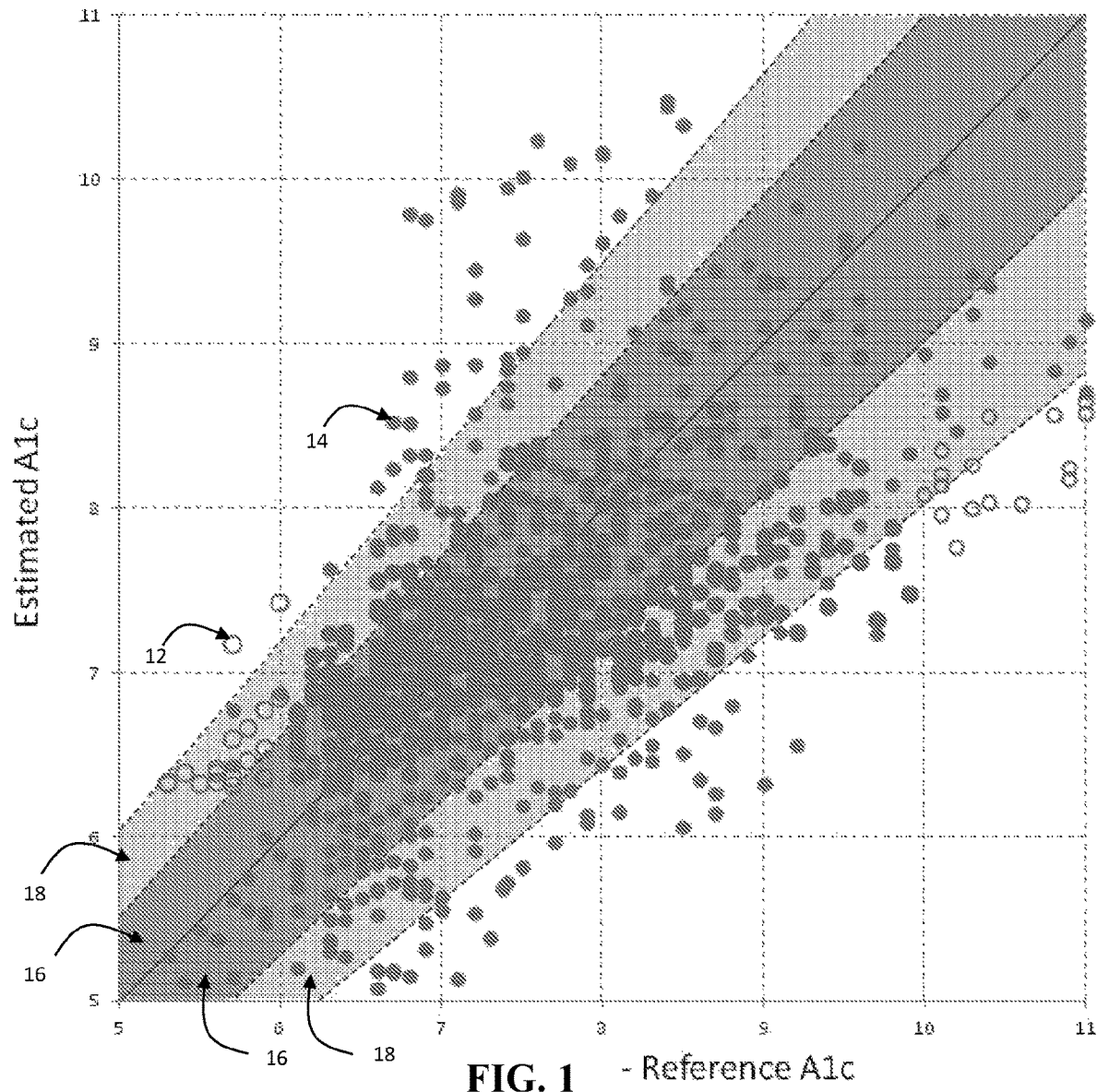
FIG. 1 is a diagram of an HbA1c error-grid for a dynamic HbA1c tracking procedure, according to one embodiment.

Data Set:

To validate the eA1c algorithm in Type 1 diabetes we used previously published data collected by 120 patients over the course of a 12-month behavioral training. As previously described, the participants in this study had average age 39.15 (SD=14.35) years, there were 51/69 males/females, the average baseline HbA1c was 7.99% (SD=1.48), and the average duration of diabetes was 20.28 (SD=12.92) years. Thirty-two percent of these subjects reported severe hypoglycemia during the year prior to the study, and 47 subjects met the criteria for hypoglycemia unawareness. During the study, subjects were instructed to perform SMBG 4-5 times per day. As a result, the average number of SMBG readings per person per day was 4.69 (SD=1.84), for a total of 188,219 readings collected during the study. HbA1c was assessed at the baseline and then approximately every 4 months, yielding 457 HbA1c values used for the analyses in this manuscript. All HbA1c values were assayed at the University of Virginia laboratory, thereby eliminating between-lab differences. Ninety-seven subjects completed the 12-month protocol and during the study their HbA1c improved to 7.58% (SD=1.08) as a result of the behavioral training procedure—an improvement that was entirely accounted for by those subjects who had baseline HbA1c>=8.0%. Overall, the behavioral training resulted in sufficiently large changes in HbA1c to allow for adequate testing of the cA1c procedure in Type 1 diabetes.

The eA1c algorithm used here is identical to the previously presented algorithm that was developed and tested in Type 2 diabetes. To reiterate, a dynamical model of hemoglobin glycation and clearance was constructed that corresponded to a first order differential equation:

$$\frac{\partial \widehat{HbA1c}}{\partial t} = -\frac{1}{\tau}(\widehat{HbA1c} - f(SMBG_t)) \quad (1)$$

where the function $f(SMBG_t)$ is a function using self-monitoring data to track glucose exposure over time. The parameter τ is fixed at r=20. The function $f(SMBG_t)$ was defined as follows:

$$f(SMBG_t) = MAX(0.99*(4.756+0.0049*mP_0(t)+CalA1c),5)$$

Where: $mP_0(t)$ is the average fasting glucose over the past 6 days (current day included) and is updated every time a new fasting glucose is measured. The function $f(SMBG_t)$ was originally calibrated using data from 7-point SMBG profiles collected approximately every month. The calibration offset is computed as:

$$CalA1c = 0.0065*\theta_1 + 0.0044*\theta_2$$

where $\theta_1$ and $\theta_2$ were the principal components of the 7-point profiles derived via standard data rotation. Because 7-point profiles were not available in the Type 1 diabetes data used here, the profiles were reconstructed as described below, after which the iterative eA1c procedure remained the same: First we compute an initial estimate:

$$eA1c(t_0) = f(SMBG_{t_0})$$

Then, we compute daily runtime estimate:

$$eA1c(t) = 0.9512*eA1c(t-1 \text{ day}) + 0.0488*f(SMBG_t)$$

The runtime estimate tracks average glycemia and presents the data in A1c units.

Reconstructing 7-Point Daily Profiles and Fasting BG: While routine SMBG data do not provide specific information whether a reading is taken before or after meal (which would be required for a 7-point profile), data density of 4-5 SMBG readings per day, which is typical for Type 1 diabetes, allows for reconstructing daily profiles taking SMBG readings from several sequential days as follows: First, the day was split into 6 time bins: (6:00-10:00)-fasting, (10:00-13:00), (13:00-16:00), (16:00-19:00), (19:00-21:00), (21:00-0:00). Surrogate for daily fasting glucose was calculated as a 3-day average of SMBG between 6:00-10:00 because these readings were not available every day. Surrogates for 7-point profiles were computed from a week of data as follows: pre-breakfast=mean of values falling in the 6:00-10:00 time bin; post-breakfast BG=maximum BG value in the 10:00-13:00 bin; pre-lunch BG=minimum BG value in that same time bin. Post-lunch, pre-post dinner, and bedtime values were determined as the averages of the (13:00-16:00), (16:00-19:00), (19:00-21:00), and (21:00-0:00) time bins, respectively.

The Hemoglobin Glycation Index (HGI) was computed as the difference between laboratory HbA1c and predicted HbA1c, where for the prediction we used surrogate fasting BG values and the exact formula previously proposed: Predicted HbA1c=0.009*Fasting BG+6.8. In order to keep the HGI results compatible with literature findings, we did not derive new HGI formula using a linear regression in this particular data set.

Data Analysis: Accuracy of the estimation procedure was evaluated in the test data set by computing mean absolute deviation (MAD), MARD, correlation between the estimate eA1c and reference HbA1c, and parameters of the distribution of the eA1c estimation error. Correlations between eA1c and HGI values were computed as well.

Results

Accuracy of eA1c in Type 1 Diabetes: In this data set, the correlation of eA1c with reference HbA1c was r=0.75, i.e. similar to the correlation previously observed in type 2 diabetes data. The mean absolute and relative deviations were MAD=0.64 HbA1c units, and MARD=7.98%. The distribution of estimation errors was as follows: 95% of eA1c values fell within ±20% from reference and 51% of all eA1c values fell within ±7% from reference corresponding to roughly half of the eA1c values within ±0.5 HbA1c units of the laboratory value. FIG. 1 presents the HbA1c error-grid plot for eA1c in Type 1 diabetes data stratified by reference HbA1c values below 6% and above 10% (open circles 12) and between 6-10% (closed circles 14). A total of 67.66% of all eA1c values fell within 10% from reference HbA1c (A-zone 16) and 95.4% fell within 20% from reference (A+B zones 16 and 18). If limited to a reportable HbA1c range (6-10%), the accuracy of eA1c was 72.8% (A-zone 16) and 98.6% (A+B zones 16 and 18). In terms of eA1c trend, there was no difference in the distributions of the HbA1c daily rate of change observed in reference HbA1c values and in eA1c values, with 95% of all estimated trends within ±0.02 HbA1c units/day from reference and 81% of all estimated trends within ±0.01 HbA1c units/day from reference.

Comparison to established linear methods: To compare the accuracy of cA1c to established linear formulas, we used two previously published linear approximations: the inverse of Nathan's formula translating the A1C assay into estimated average glucose values and the formula previously introduced by Hempe, which uses only fasting BG readings to estimate HbA1c. The present inventors kept unchanged the coefficient introduced in the original publications and computed MAD, MARD, and correlations with reference HbA1c of eA1c and the two linear estimates. Table 1 summarizes the results:

TABLE 1 comparison of performances between eA1c and static methods based on fasting glucose

|  | eA1c | Nathan's formula | Hempe's formula |
| --- | --- | --- | --- |
| MAD | 0.64 | 0.87 | 1.05 |
| MARD | 7.98% | 11.40% | 14.5% |
| Correlation | 0.75 | 0.65 | 0.54 |

Robustness analysis: Stratifying the data by reference HbA1c, the dynamical method was most accurate in the 7-8% HbA1c range, with minimal bias and 4.6% MARD, as illustrated in Table 2. Bias of eA1c was mostly below 1% HbA1c and MARD≤10%, but for the 9-10 categories, in which we had limited data. Stratifying the data by eA1c and not reporting values below 6% and above 10% resulted in HbA1c biases between −0.66% and 0.07% and MARDs between 6.74% and 10.3%. Performance at the initial eA1c for each subject was similar to overall performance (MARD 8.49% vs. 7.98%; MAD 0.71 vs. 0.65). The larger initial MAD was not associated with the initial HbA1c values being significantly higher than subsequent values (7.71% vs. 7.59%, ns).

TABLE 2

Performance of eAc1 and Nathan's formula by HbA1c and eA1c ranges

| reference HbA1c ranges | | 6-7 | 7-8 | 8-9 | 9-10 |
| --- | --- | --- | --- | --- | --- |
| Number of pairs | | 136 | 161 | 103 | 33 |
| MARD | eA1c | 6.4% | 4.6% | 9.4% | 15.3% |
|  | Nathan's formula | 11.1% | 11.2% | 12.8% | 11.2% |
| MAD | eA1c | 0.42 | 0.34 | 0.79 | 1.44 |
|  | Nathan's formula | 0.73 | 0.84 | 1.07 | 1.05 |
| Bias | eA1c | 0.38 | −0.11 | −0.74 | −1.44 |
|  | Nathan's formula | −0.12 | −0.05 | −0.36 | −0.74 |
| eA1c ranges | | 6-7 | 7-8 | 8-9 | 9-10 |
| Number of pairs | | 129 | 274 | 66 | 1 |
| MARD | eA1c | 6.7% | 8.0% | 10.3% | NA |
|  | Nathan's formula | 10.9% | 11.0% | 13.9% | NA |
| MAD | eA1c | 0.44 | 0.64 | 0.99 | NA |
|  | Nathan's formula | 0.75 | 0.85 | 1.20 | NA |
| Bias | eA1c | 0.07 | −0.31 | −0.66 | NA |
|  | Nathan's formula | −0.65 | −0.20 | 0.44 | NA |

Relationship between HGI and eA1c: To determine whether the calibration factors of eA1c can predict the difference between lab HbA1c and Hempe's linear model, a regression of HGI was performed with the calibration factors $\theta_1$ and $\theta_2$, which resulted in a highly significant linear model (F=158.4, p<0.0001) and Multiple R=0.63 ($R^2$=0.40). This suggests that HGI can be approximated by the following linear combination of the eA1c calibration factors: HGI=0.007552*$\theta_1$+0.007645*$\theta_2$−3.154. In addition, the direct correlation between HGI and eA1c was 0.51, p<0.001. The low vs. moderate-high HGI groups defined by Hempe et al as HGI≤−0.520, vs. HGI>−0.520 were predicted by discriminant analysis using $\theta_1$ and $\theta_2$, which resulted in a highly significant discriminant model (Chi-square=133.1, p<0.0001) and correct overall classification of 73%. The correct classification of the Low-HGI group was 78.5% and of the Moderate-High HGI subgroup was 63.4%. We should note that the distribution of low-moderate-high HGI in this population was different than the distribution in the original paper where these subgroups were defined by the sample tertiles: here we observed 63%, 18%, 19% low, moderate, high HGI, respectively. Thus, the biological variation causing discrepancies between HbA1c and its linear estimates from SMBG data can be at least partially explained by the eA1c calibration factors.

DISCUSSION

Without changing a previously reported Dynamical Tracking eA1c Algorithm developed in a population of people with Type 2 diabetes, the present inventors tested its ability to track HbA1c in a group of 120 patients with Type 1 Diabetes who were observed over a year as part of a behavioural intervention study. The present inventors have confirmed that the eA1c procedure works as designed and produces results similar to those achieved in the original Type 2 population. The slight increase in MARD observed here is attributed to the significant departure of the structure of the data in hand from the data structure in our original studies. Specifically, the original algorithm design was based on daily fasting BGs and occasional (monthly) 7-point BG profiles taken at pre-post meal times and used for calibration of the fasting eA1c trace. Here, 7-point profiles were not available and there was no indication which SMBG readings were fasting, pre- or post-meal. To compensate for this data deficiency, we reconstructed surrogate daily profiles using time bins that were for all subjects. The time bins were filled up with available SMBG readings acquired over 7 consecutive days of observation (3 days for fasting BG) and were then used in the exact same way as the 7-point profiles of the original algorithm. In addition to being necessary in this data set, such an approach allows the collection of structured 7-point daily profiles (which was found inconvenient by some users) to be abandoned and replaced by appropriate binning of routine SMBG data, provided that sufficient BG readings are collected to aggregate a profile over time (e.g. 7 days). Moreover, structured "profile days" would become unnecessary and the profiles can be constructed and tracked on weekly basis. Given the need for a calibration profile approximately once a month as established by our original work, we can now speculate that routine SMBG yielding 1 week out of 5 weeks with good "profile-grade" data would be sufficient to run the eA1c estimation procedure without structured profile entries.

Despite the arbitrary interpretation of the available SMBG data, the eA1c procedure held its accuracy. Thus, the findings of this manuscript can be viewed not only as a validation of the eA1c estimate in Type 1 diabetes, but also as a test of the robustness of the procedure under extreme unstructured data conditions. The key to this level of robustness is our conceptually new approach to the retrieval of SMBG data: using compartmental modelling, we constructed a two-step algorithm that includes real-time eA1c from fasting glucose readings, updated with any new incoming fasting SMBG data point, and initialization and calibration of the estimated HbA1c trace with daily SMBG profiles taken approximately every month. The model was originally developed using training data, then fixed and applied to independent test data, both of which were collected in Type 2 diabetes. Now the eA1c is translated without any further changes to Type 1 diabetes as well.

As in the present inventors' previous paper, they compared the eA1c procedure to established linear methods and verified that its accuracy in approximating laboratory HbA1c was still higher. We took this comparison one step further and evaluated the relationship between eA1c and the HGI (haemoglobin glycation index) in this population using the original HGI formula and proposed cutoff points. We found that the two factors used to calibrate the eA1c algorithm are highly (and equally) related to the HGI. Used in a regression or discriminant predictive models, these factors resulted not only in statistically significant relationships, but also in 73% accurate classification rate of low- vs. moderate-high HGI groups. This would suggest that these factors (which are based on routine SMBG data alone) could be used as surrogate classifiers for low- vs. moderate-high HGI. Given the clinical significance of the HGI for both prediction of complications of diabetes and prediction of the effectiveness of diabetes treatment, the ability to track HGI state in real time from routine SMBG opens new possibilities for patient assessment and fine-tuning of treatment aggressiveness. Such an application of the eA1c calibration factors is consistent with the original intent of the eA1c procedure: it is a method for tracking changes in average glycemia in-between laboratory HbA1c assessments.

Figure 2:
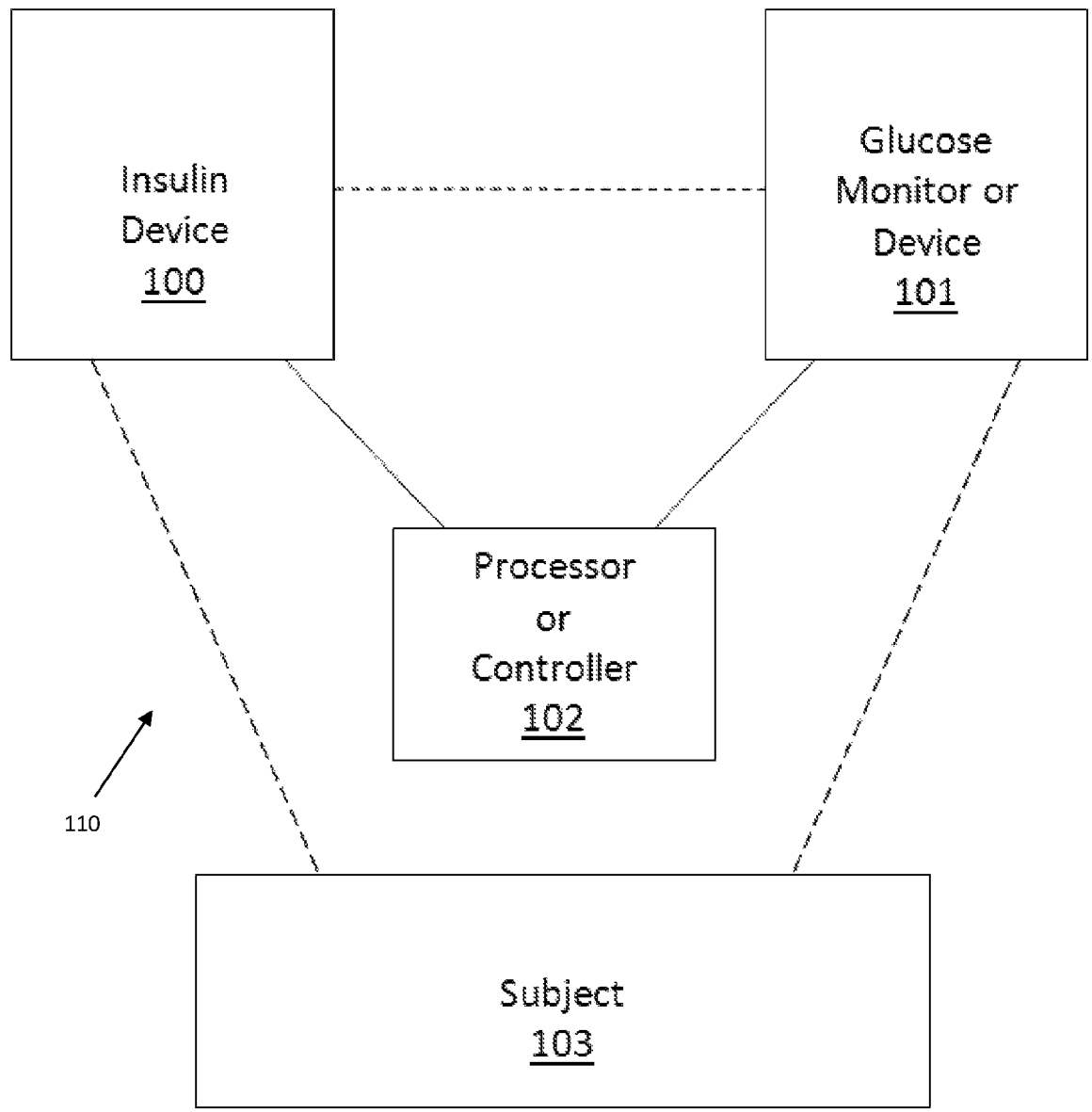
FIG. 2 illustrates a functional block diagram of a system for tracking changes in average glycaemia in diabetics, according to one embodiment.

FIG. 2 is a high level functional block diagram of an embodiment of a system 110 for tracking changes in average glycaemia in diabetics.

As shown in FIG. 2, a processor or controller 102 communicates with the glucose monitor or device 101, and optionally the insulin device 100. The glucose monitor or device 101 communicates with the subject 103 to monitor glucose levels of the subject 103. The processor or controller 102 is configured to perform the required calculations. Optionally, the insulin device 100 communicates with the subject 103 to deliver insulin to the subject 103. The processor or controller 102 is configured to perform the required calculations. The glucose monitor 101 and the insulin device 100 may be implemented as a separate device or as a single device. The processor 102 can be implemented locally in the glucose monitor 101, the insulin device 100, or a standalone device (or in any combination of two or more of the glucose monitor, insulin device, or a stand along device). The processor 102 or a portion of the system can be located remotely such that the device is operated as a telemedicine device.

Figure 3A:
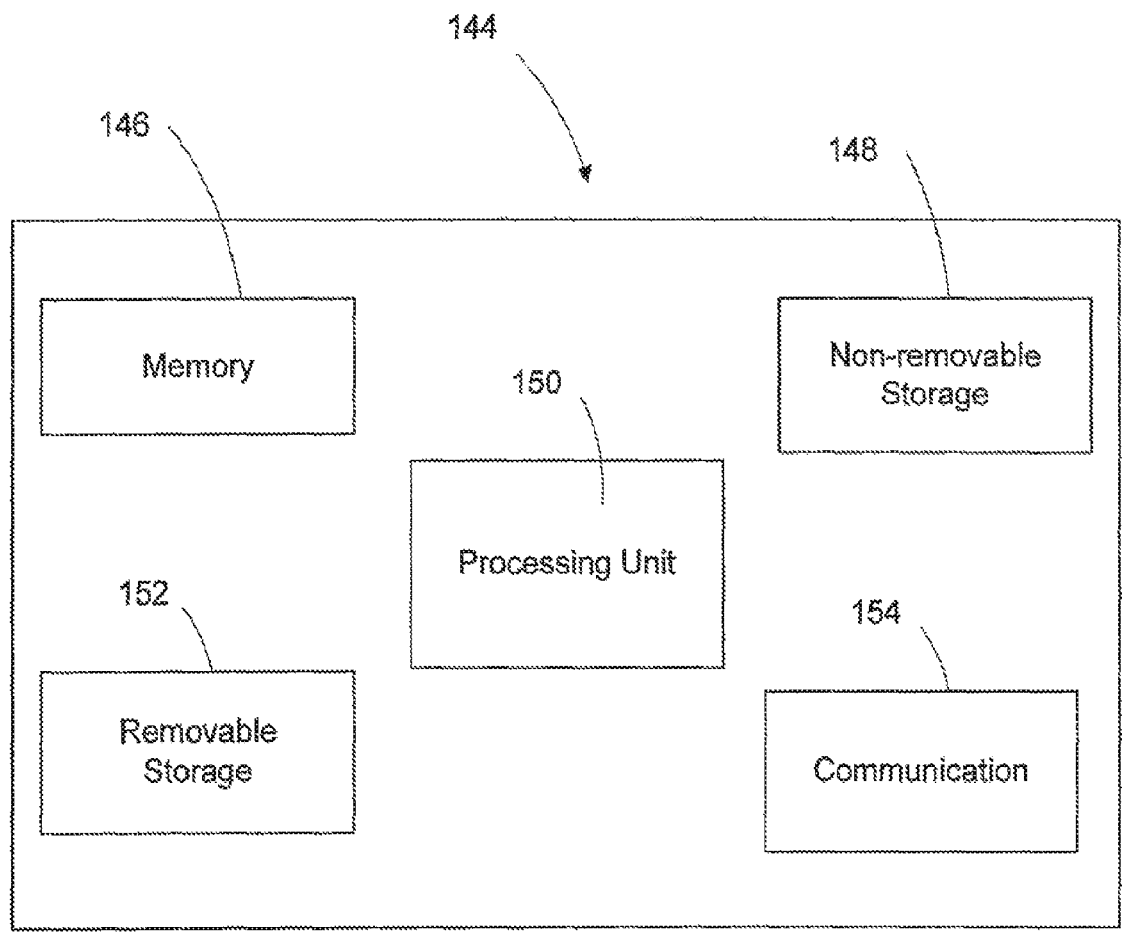
FIG. 3A illustrates a block diagram of an example computing device.

Referring to FIG. 3A, in its most basic configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

Figure 3B:
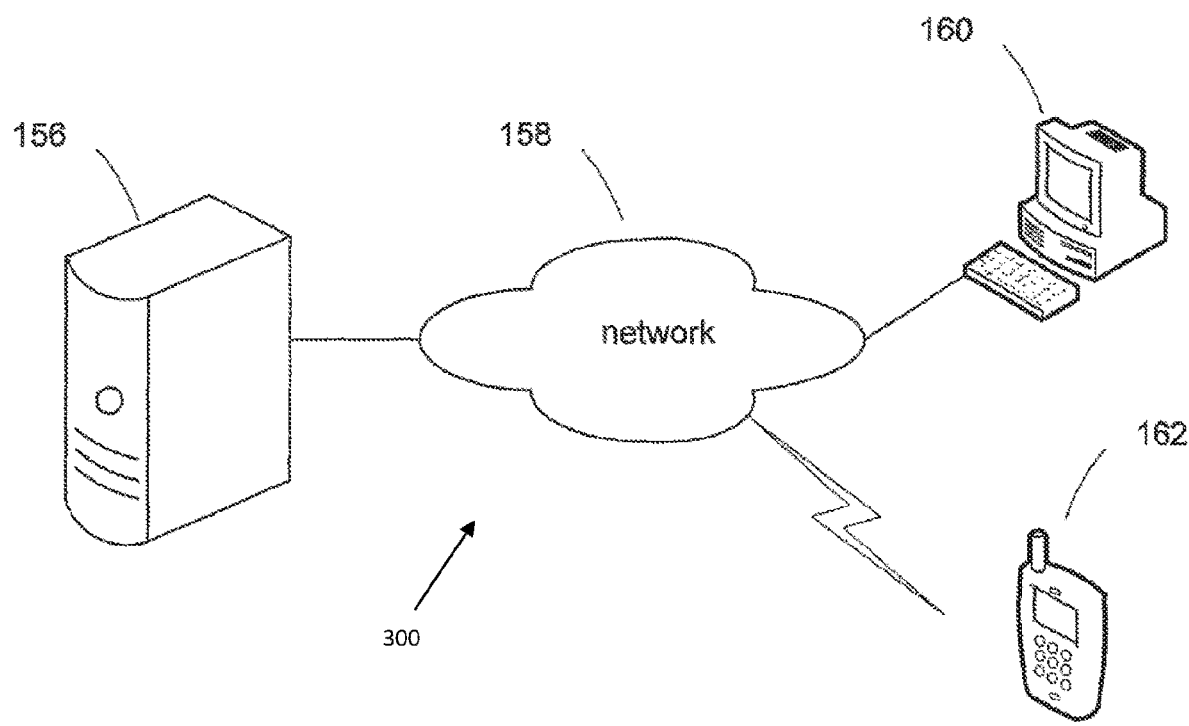
FIG. 3B illustrates an example network system in which embodiments of the example system of FIG. 2 can be implemented.

In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections. As a way of example, FIG. 3B illustrates a network system 300 in which embodiments of the example system 110 can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non portable devices) with combinations of such features). In an embodiment, it should be appreciated that the module listed as 156 may be glucose monitor device. In an embodiment, it should be appreciated that the module listed as 156 may be a glucose monitor device and/or an insulin device. Any of the components shown or discussed with FIG. 3B may be multiple in number. The embodiments of the invention can be implemented in anyone of the devices of the system. For example, execution of the instructions or other desired processing can be performed on the same computing device that is anyone of 156, 160, and 162. Alternatively, an embodiment of the invention can be performed on different computing devices of the network system. For example, certain desired or required processing or execution can be performed on one of the computing devices of the network (e.g. server 156 and/or glucose monitor device), whereas other processing and execution of the instruction can be performed at another computing device (e.g. terminal 160) of the network system, or vice versa. In fact, certain processing or execution can be performed at one computing device (e.g. server 156 and/or glucose monitor device); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

Figure 4:
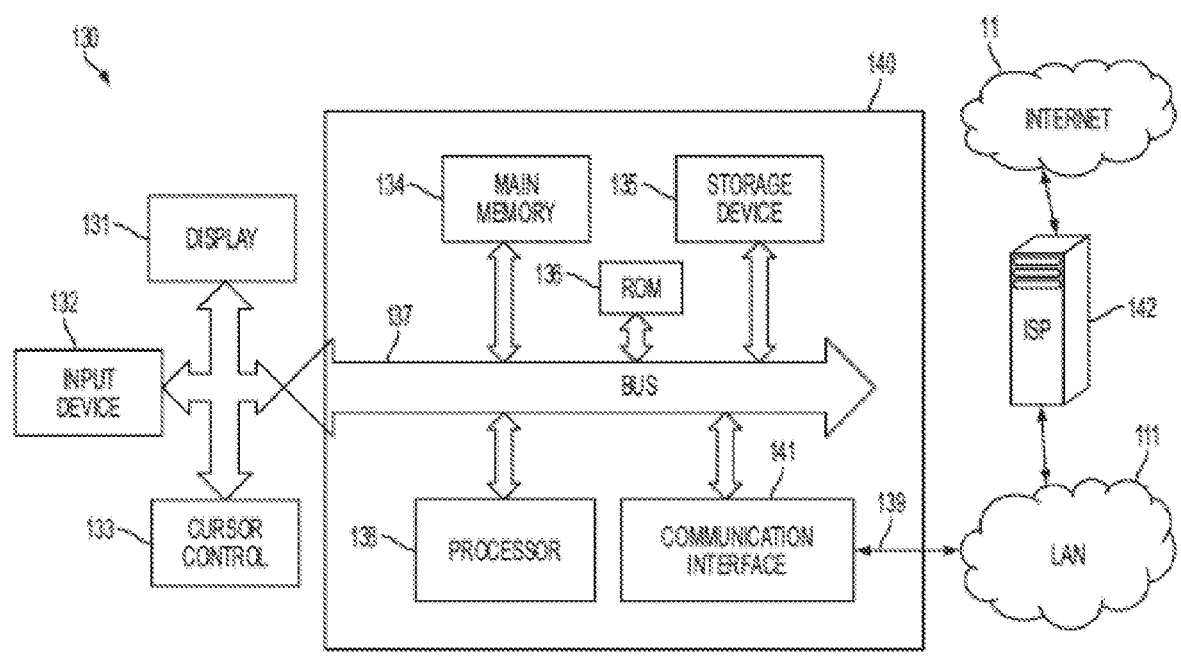
FIG. 4 is a block diagram that illustrates an example system including a computer system and the associated Internet connection upon which an embodiment of the example system of FIG. 2 may be implemented.

FIG. 4 is a block diagram that illustrates a system 130 including a computer system 140 and the associated Internet 11 connection upon which an embodiment of the example system 110 may be implemented. Such configuration is typically used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 4. The system 140 may be used as a portable electronic device such as a notebook/laptop computer, a media player (e.g., MP3 based or video player), a cellular phone, a Personal Digital Assistant (PDA), a glucose monitor device, an insulin delivery device, an image processing device (e.g., a digital camera or video recorder), and/or any other handheld computing devices, or a combination of any of these devices. Note that while FIG. 4 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used. The computer system of FIG. 4 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hardwired circuitry may be used in place of or in combination with software instructions to implement the arrangement. Thus, embodiments of the invention are not limited to any specific combination of hardware circuitry and software.

The term "computer-readable medium" (or "machine-readable medium") as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (Feb. 20, 2004), which is incorporated in its entirety for all purposes as if fully set forth herein.

Wireless links may also be implemented. In any such implementation, communication interface 141 sends and receives electrical, electromagnetic or optical signals that carry digital data streams representing various types of information.

Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

The concept of real-time estimation of HBA1c from self-monitoring data has been developed. The concept of testing eA1c in Type 1 diabetes and assessing its relationship to the hemoglobin glycation index (HGI) has been established. As seen from the algorithm and methodology requirements discussed herein, the procedure is readily applicable into devices with limited processing power, such as hoe SMBG meters, and may be implemented and utilized with the related processors, networks, computer systems, internet, and components and functions according to the schemes disclosed herein.

Figure 5:
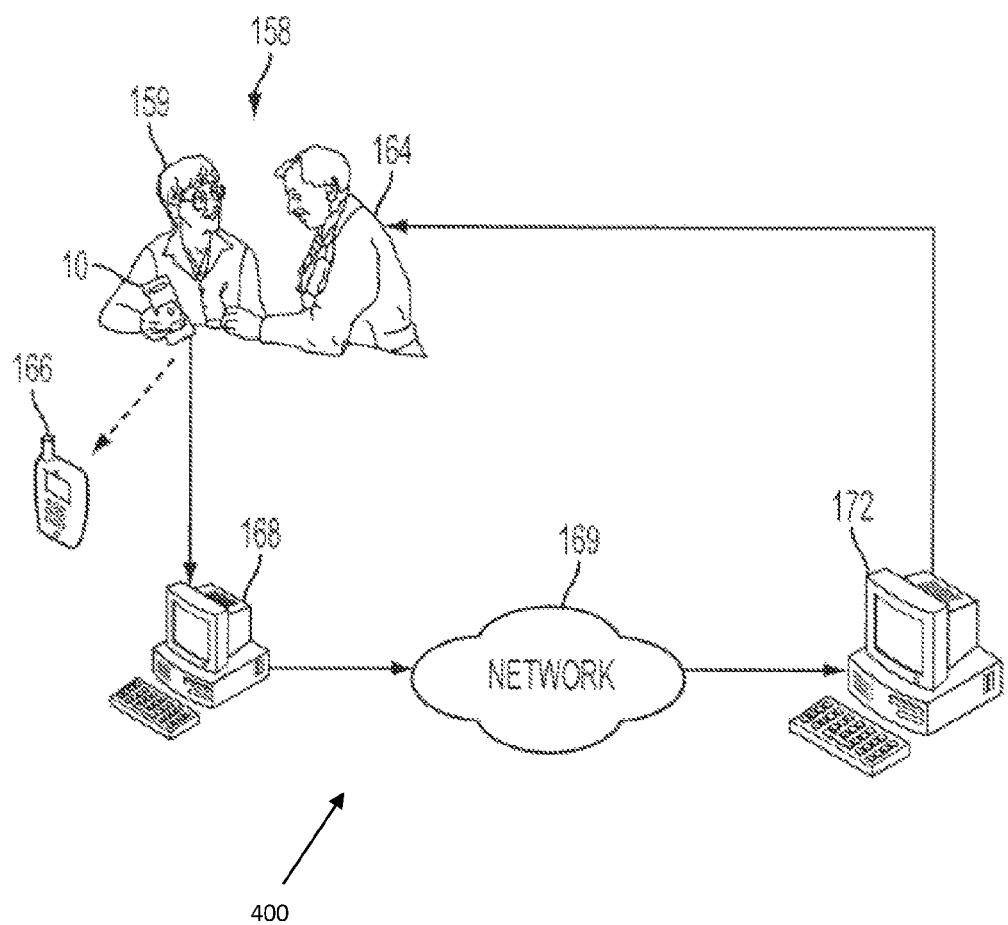
FIG. 5 illustrates an example system in which one or more embodiments of the example system of FIG. 2 can be implemented using a network.

FIG. 5 illustrates a system in which one or more embodiments of the example system 110 can be implemented using a network, or portions of a network or computers. However, it should be appreciated that, in an example embodiment, a glucose device may be practiced without a network.

FIG. 5 diagrammatically illustrates an exemplary system 500 in which examples of the system 110 can be implemented. In an embodiment the glucose monitor may be implemented by the subject (or patient) locally at home or other desired location. However, in an alternative embodiment it may be implemented in a clinic setting or assistance setting. For instance, referring to FIG. 5, a clinic setup 158 provides a place for doctors (e.g. 164) or clinician/assistant to diagnose patients (e.g. 159) with diseases related with glucose and related diseases and conditions. A glucose monitoring device 10 can be used to monitor and/or test the glucose levels of the patient—as a standalone device. It should be appreciated that while only glucose monitor device 10 is shown in the figure, the system of the invention and any component thereof may be used in the manner depicted by FIG. 5. The system or component may be affixed to the patient or in communication with the patient as desired or required. For example the system or combination of components thereof—including a glucose monitor device 10 (or other related devices or systems such as a controller, and/or an insulin pump, or any other desired or required devices or components)—may be in contact, communication or affixed to the patient through tape or tubing (or other medical instruments or components) or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions or modeling. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring, modeling and/or accuracy enhancement for glucose centers, due to the importance of the glucose sensors.

Examples of the invention can also be implemented in a standalone computing device associated with the target glucose monitoring device. An exemplary computing device (or portions thereof) in which examples of the invention can be implemented is schematically illustrated in FIG. 3A.

CONCLUSIONS

The cA1c procedure developed in Type 2 diabetes to track in real time changes in average glycemia and present the results in HbA1c-equivalent units has now been validated in Type 1 diabetes. In the process, two new findings have emerged, such as but not limited thereto: (1) Appropriate aggregation of routine SMBG data into time bins would eliminate the need for taking structured 7-point SMBG profiles once a month, and (2) The calibration factors of the eA1c estimation procedure are highly predictive of the Hemoglobin Glycation Index, which opens possibilities for tracking the clinically-relevant HGI in real time as well.

REFERENCES

The following patents, applications and publications as listed below and throughout this document are hereby incorporated by reference in their entirety herein.

1. Kovatchev B P, Flacke F, Sieber J, Breton M D. Accuracy and Robustness of Dynamical Tracking of Average Glycemia (A1c) to Provide Real-Time Estimation of Hemoglobin A1c Using Routine Self-Monitored Blood Glucose Data. Diabetes Technol Ther 2014; 16:303-309.
2. Nathan D M, Kuenen J, Borg R, Zheng H, Schoenfeld D, Heine R J: Translating the A1C assay into estimated average glucose values. Diabetes Care 2008; 31:1473-1478.
3. Hamren B, Bjork E, Sunzel M, Karlsson M: Models for plasma glucose, HbA1c, and hemoglobin interrelationships in patients with type 2 diabetes following tesaglitazar treatment. Clin Pharmacol Ther 2008; 84:228-235.
4. Heisler M, Piette J D, Spencer M, Kieffer E, Vijan S: The relationship between knowledge of recent HbA1c values and diabetes care understanding and self-management. Diabetes Care 2005; 28:816-822.
5. Polneau S V, Lasserre V, Fonfrede M, Delattre J, Benazeth S: A different approach to analyzing age-related HbA1c values in non-diabetic subjects. Clinical Chemistry and Laboratory Medicine 2004; 42:423-428.
6. Landgraf R: The relationship of postprandial glucose to HbA1c. Diabetes Metab Res Rev 2004; 20 Suppl 2:S9-S12.
7. Kahrom M: An innovative mathematical model: a key to the riddle of HbA(1c). Int J Endocrinol 2010. 10.1155/2010/481326. Epub August 29.
8. Ollerton R L, Luzio S D, Owens D R: Contribution of fasting and postprandial plasma glucose to HbA1c. Diabet Med 2005; 22:954-955.
9. Osterman-Golkar S M, Vesper H W: Assessment of the relationship between glucose and A1c using kinetic modeling. J Diabetes Complications 2006; 20:285-294.
10. Trevino G: On the weighted-average relationship between plasma glucose and HbA1c. Diabetes Care 2006; 29:466-467.
11. Trevino G: A nonlinear relation between glucose and A1c. Diabetes Res Clin Pract 2008; 79:e14.
12. Hempe J M, Soros A A, Chalew S A. Estimated Average Glucose and Self-Monitored Mean Blood Glucose Are Discordant Estimates of Glycemic Control. Diabetes Care 2010; 33:1449-1451.
13. McCarter R J, Hempe J M, Gomez R, Chalew S A. Biological Variation in HbA1c Predicts Risk of Retinopathy and Nephropathy in Type 1 Diabetes. Diabetes Care 2004; 27:1259-1264.
14. Hempe J M, Liu S, Myers L, McCarter R J, Buse J B, and Fonseca V. The hemoglobin glycation index identifies subpopulations with harms or benefits from intensive treatment in the ACCORD trial. Diabetes Care Publish Ahead of Print, 2015. DOI: 10.2337/dc14-1844
15. Kovatchev B P, Mendosa P, Anderson S, Hawley J S, Ritterband L M, Gonder-Frederick L: Effect of automated bio-behavioral feedback on the control of type 1 diabetes. Diabetes Care 2011; 34:302-307.

The following patents, applications and publications as listed below and throughout this document are hereby incorporated by reference in their entirety herein. It should be appreciated that various aspects of embodiments of the present method, system, devices, article of manufacture, computer readable medium, and compositions may be implemented with the following methods, systems, devices, article of manufacture, computer readable medium, and compositions disclosed in the following U.S. Patent Applications, U.S. Patents, and PCT International Patent Applications and are hereby incorporated by reference herein and co-owned with the assignee (and which are not admitted to be prior art with respect to the present invention by inclusion in this section):

A. U.S. patent application Ser. No. 14/419,375 entitled "Computer Simulation for Testing and Monitoring of Treatment Strategies for Stress Hyperglycemia", filed Feb. 3, 2015.

B. International Patent Application No. PCT/US2013/053664 entitled "Computer Simulation for Testing and Monitoring of Treatment Strategies for Stress Hyperglycemia", filed Aug. 5, 2013; International Patent Application Publication No. WO 2014/022864, Feb. 6, 2014. International Patent Application No. PCT/US2015/010167 entitled "Central Data Exchange Node For System Monitoring and Control of Blood Glucose Levels in Diabetic Patients", filed Jan. 5, 2015.

C. International Patent Application No. PCT/US2014/045393 entitled "Simulation of Endogenous and Exogenous Glucose/Insulin/Glucagon Interplay in Type 1 Diabetic Patients", filed Jul. 3, 2014; International Patent Application Publication No. WO 2015/003124, Jan. 8, 2015.

D. U.S. patent application Ser. No. 14/266,612 entitled "Method, System and Computer Program Product for Real-Time Detection of Sensitivity Decline in Analyte Sensors", filed Apr. 30, 2014; U.S. Patent Application Publication No. 2014/0244216, Aug. 28, 2014.

E. U.S. patent application Ser. No. 13/418,305 entitled "Method, System and Computer Program Product for Real-Time Detection of Sensitivity Decline in Analyte Sensors", filed Mar. 12, 2012; U.S. Pat. No. 8,718,958, issued May 6, 2014.

F. International Patent Application No. PCT/US2007/082744 entitled "Method, System and Computer Program Product for Real-Time Detection of Sensitivity Decline in Analyte Sensors", filed Oct. 26, 2007; International Patent Application Publication No. WO/2008/052199, May 2, 2008.

G. U.S. patent application Ser. No. 11/925,689 entitled "Method, System and Computer Program Product for Real-Time Detection of Sensitivity Decline in Analyte Sensors", filed Oct. 26, 2007; U.S. Pat. No. 8,135,548, issued Mar. 13, 2012.

H. U.S. patent application Ser. No. 14/241,383 entitled "Method, System and Computer Readable Medium for Adaptive Advisory Control of Diabetes", filed Feb. 26, 2014.

I. International Patent Application No. PCT/US2012/052422 entitled "Method, System and Computer Readable Medium for Adaptive Advisory Control of Diabetes", filed Aug. 26, 2012; International Patent Application Publication No. WO 2013/032965, Mar. 7, 2013.

J. International Patent Application No. PCT/US2014/017754 entitled "Method and System for Model-Based Tracking of Changes in Average Glycemia in Diabetes", filed Feb. 21, 2014; International Patent Application Publication No. WO 2014/130841, Aug. 28, 2014.

K. U.S. patent application Ser. No. 14/128,922 entitled "Unified Platform For Monitoring and Control of Blood Glucose Levels in Diabetic Patients", filed Dec. 23, 2013; U.S. Patent Application Publication No. 2015/0018633, Jan. 15, 2015.

L. International Patent Application No. PCT/US2012/043910 entitled "Unified Platform For Monitoring and Control of Blood Glucose Levels in Diabetic Patients", filed Jun. 23, 2012; International Patent Application Publication No. WO 2012/178134, Dec. 27, 2012.

M. U.S. patent application Ser. No. 14/128,811 entitled "Methods and Apparatus for Modular Power Management and Protection of Critical Services in Ambulatory Medical Devices", filed Dec. 23, 2013; U.S. Patent Application Publication No. 2014/0215239, Jul. 31, 2014.

N. International Patent Application No. PCT/US2012/043883 entitled "Methods and Apparatus for Modular Power Management and Protection of Critical Services in Ambulatory Medical Devices", filed Jun. 22, 2012; International Patent Application Publication No. WO 2012/178113, Dec. 27, 2012.

O. U.S. patent application Ser. No. 14/015,831 entitled "CGM-Based Prevention of Hypoglycemia Via Hypoglycemia Risk Assessment and Smooth Reduction Insulin Delivery", filed Aug. 30, 2013; U.S. Patent Application Publication No. 2014/0046159, Feb. 13, 2014.

P. U.S. patent application Ser. No. 13/203,469 entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013.

Q. International Patent Application No. PCT/US2010/025405 entitled "CGM-Based Prevention of Hypoglycemia via Hypoglycemia Risk Assessment and Smooth Reduction Insulin Delivery", filed Feb. 25, 2010; International Patent Application Publication No. WO 2010/099313, Sep. 2, 2010.

R. International Patent Application No. PCT/US2013/042745 entitled "Insulin-Pramlintide Compositions and Methods for Making and Using Them", filed May 24, 2013; International Application Publication No. WO 2013/177565, Nov. 28, 2013.

S. U.S. patent application Ser. No. 13/637,359 entitled "Method, System, and Computer Program Product for Improving the Accuracy of Glucose Sensors Using Insulin Delivery Observation in Diabetes", filed Sep. 25, 2012; U.S. Patent Application Publication No. 2013/0079613, Mar. 28, 2013.

T. International Patent Application No. PCT/US2011/029793 entitled "Method, System, and Computer Program Product for Improving the Accuracy of Glucose Sensors Using Insulin Delivery Observation in Diabetes", filed Mar. 24, 2011; International Patent Application Publication No. WO 2011/119832, Sep. 29, 2011.

U. U.S. patent application Ser. No. 13/634,040 entitled "Method and System for the Safety, Analysis, and Supervision of Insulin Pump Action and Other Modes of Insulin Delivery in Diabetes", filed Sep. 11, 2012; U.S. Patent Application Publication No. 2013/0116649, May 9, 2013.

V. International Patent Application No. PCT/US2011/028163 entitled "Method and System for the Safety, Analysis, and Supervision of Insulin Pump Action and Other Modes of Insulin Delivery in Diabetes", filed Mar. 11, 2011; International Patent Application Publication No. WO 2011/112974, Sep. 15, 2011. U.S. patent application Ser. No. 13/394,091 entitled "Tracking the Probability for Imminent Hypoglycemia in Diabetes from Self-Monitoring Blood Glucose (SMBG) Data", filed Mar. 2, 2012; U.S. Patent Application Publication No. 2012/0191361, Jul. 26, 2012.

W. International Patent Application No. PCT/US2010/047711 entitled "Tracking the Probability for Imminent Hypoglycemia in Diabetes from Self-Monitoring Blood Glucose (SMBG) Data", filed Sep. 2, 2010; International Patent Application Publication No. WO 2011/028925, Mar. 10, 2011.

X. U.S. patent application Ser. No. 13/393,647 entitled "System, Method and Computer Program Product for Adjustment of Insulin Delivery (AID) in Diabetes Using Nominal Open-Loop Profiles", filed Mar. 1, 2012; U.S. Patent Application Publication No. 2012/0245556, Sep. 27, 2012. International Patent Application No. PCT/US2010/047386 entitled "System, Method and Computer Program Product for Adjustment of Insulin Delivery (AID) in Diabetes Using Nominal Open-Loop Profiles", filed Aug. 31, 2010; International Application Publication No. WO 2011/028731, Mar. 10, 2011.

Y. U.S. patent application Ser. No. 13/380,839 entitled "System, Method, and Computer Simulation Environment for In Silico Trials in Pre-Diabetes and Type 2 Diabetes", filed Dec. 25, 2011; U.S. Patent Application Publication No. 2012/0130698, May 24, 2012.

Z. International Patent Application No. PCT/US2010/040097 entitled "System, Method, and Computer Simulation Environment for In Silico Trials in Prediabetes and Type 2 Diabetes", filed Jun. 25, 2010; International Application Publication No. WO 2010/151834, Dec. 29, 2010.

AA. U.S. patent application Ser. No. 13/322,943 entitled "System Coordinator and Modular Architecture for Open-Loop and Closed-Loop Control of Diabetes", filed Nov. 29, 2011; U.S. Patent Application Publication No. 2012/0078067, Mar. 29, 2012.

BB. International Patent Application No. PCT/US2010/036629 entitled "System Coordinator and Modular Architecture for Open-Loop and Closed-Loop Control of Diabetes", filed May 28, 2010; International Patent Application Publication No. WO 2010/138848, Dec. 2, 2010.

CC. U.S. patent application Ser. No. 13/131,467 entitled "Method, System, and Computer Program Product for Tracking of Blood Glucose Variability in Diabetes", filed May 26, 2011; U.S. Patent Application Publication No. 2011/0264378, Oct. 27, 2011.

DD. International Patent Application No. PCT/US2009/065725 entitled "Method, System, and Computer Program Product for Tracking of Blood Glucose Variability in Diabetes", filed Nov. 24, 2009; International Patent Application Publication No. WO 2010/062898, Jun. 3, 2010.

EE. U.S. patent application Ser. No. 12/975,580 entitled "Method, System, and Computer Program Product for the Evaluation of Glycemic Control in Diabetes from Self-Monitoring Data", filed Dec. 22, 2010; U.S. Patent Application Publication No. 2012/0004512, Jan. 5, 2012.

FF. U.S. patent application Ser. No. 11/305,946 entitled "Method, System, and Computer Program Product for the Evaluation of Glycemic Control in Diabetes from Self-Monitoring Data", filed Dec. 19, 2005; U.S. Pat. No. 7,874,985, issued Jan. 25, 2011.

GG. U.S. patent application Ser. No. 10/240,228 entitled "Method, System, and Computer Program Product for the Evaluation of Glycemic Control in Diabetes from Self-Monitoring Data", filed Sep. 26, 2002; U.S. Pat. No. 7,025,425, issued Apr. 11, 2006.

HH. International Patent Application No. PCT/US2001/009884 entitled "Method, System, and Computer Program Product for the Evaluation of Glycemic Control in Diabetes", filed Mar. 29, 2001; International Application Publication No. WO 2001/72208, Oct. 4, 2001.

II. U.S. patent application Ser. No. 12/674,348 entitled "Method, Computer Program Product and System for Individual Assessment of Alcohol Sensitivity", filed Feb. 19, 2010; U.S. Patent Application Publication No. 2011/0264374, Oct. 27, 2011.

JJ. U.S. patent application Ser. No. 12/665,149 entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; U.S. Patent Application Publication No. 2010/0198520, Aug. 5, 2010.

KK. International Patent Application No. PCT/US2008/069416 entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; International Patent Application Publication No. WO 2009/009528, Jan. 15, 2009.

LL. U.S. patent application Ser. No. 12/664,444 entitled "Method, System and Computer Simulation Environment for Testing of Monitoring and Control Strategies in Diabetes", filed Dec. 14, 2009; U.S. Patent Application Publication No. 2010/0179768, Jul. 15, 2010.

MM. International Patent Application No. PCT/US2008/067725 entitled "Method, System and Computer Simulation Environment for Testing of Monitoring and Control Strategies in Diabetes", filed Jun. 20, 2008; International Patent Application Publication No. WO 2008/157781, Dec. 24, 2008.

NN. U.S. patent application Ser. No. 12/516,044 entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013.

OO. International Patent Application No. PCT/US2007/085588 entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; International Patent Application Publication No. WO2008/067284, Jun. 5, 2008.

PP. U.S. patent application Ser. No. 12/159,891 entitled "Method, System and Computer Program Product for Evaluation of Blood Glucose Variability in Diabetes from Self-Monitoring Data", filed Jul. 2, 2008; U.S. Patent Application Publication 2009/0171589, Jul. 2, 2009.

QQ. International Patent Application No. PCT/US2007/000370 entitled "Method, System and Computer Program Product for Evaluation of Blood Glucose Variability in Diabetes from Self-Monitoring Data", filed Jan. 5, 2007; International Application Publication No. WO 2007/081853, Jul. 19, 2007.

RR. U.S. patent application Ser. No. 12/065,257 entitled "Accuracy of Continuous Glucose Sensors", filed Feb. 28, 2008; U.S. Patent Application Publication No. 2008/0314395, Dec. 25, 2008.

SS. International Patent Application No. PCT/US2006/033724 entitled "Method for Improvising Accuracy of Continuous Glucose Sensors and a Continuous Glucose Sensor Using the Same", filed Aug. 29, 2006; International Application Publication No. WO 2007027691, Mar. 8, 2007.

TT. U.S. patent application Ser. No. 11/943,226 entitled "Systems, Methods and Computer Program Codes for Recognition of Patterns of Hyperglycemia and Hypoglycemia, Increased Glucose Variability, and Ineffective Self-Monitoring in Diabetes", filed Nov. 20, 2007; U.S. Patent Application Publication No. 2008/0154513, Jun. 26, 2008.

UU. U.S. patent application Ser. No. 11/578,831 entitled "Method, System and Computer Program Product for Evaluating the Accuracy of Blood Glucose Monitoring Sensors/Devices", filed Oct. 18, 2006; U.S. Pat. No. 7,815,569, issued Oct. 19, 2010.

VV. International Patent Application No. US2005/013792 entitled "Method, System and Computer Program Product for Evaluating the Accuracy of Blood Glucose Monitoring Sensors/Devices", filed Apr. 21, 2005; International Application Publication No. WO 2005/106017, Nov. 10, 2005.

WW. U.S. patent application Ser. No. 10/524,094 entitled "Method, System, And Computer Program Product For The Processing Of Self-Monitoring Blood Glucose (SMBG) Data To Enhance Diabetic Self-Management", filed Feb. 9, 2005; U.S. Pat. No. 8,538,703, issued Sep. 17, 2013

XX. International Patent Application No. PCT/US2003/025053 entitled "Managing and Processing Self-Monitoring Blood Glucose", filed Aug. 8, 2003; International Application Publication No. WO 2001/72208, Oct. 4, 2001.

YY. International Patent Application No. PCT/US2002/005676 entitled "Method and Apparatus for the Early Diagnosis of Subacute, Potentially Catastrophic Illness", filed Feb. 27, 2002; International Application Publication No. WO 2002/67776, Sep. 6, 2002.

ZZ. U.S. patent application Ser. No. 10/069,674 entitled "Method and Apparatus for Predicting the Risk of Hypoglycemia", filed Feb. 22, 2002; U.S. Pat. No. 6,923,763, issued Aug. 2, 2005.

AAA. International Patent Application No. PCT/US00/22886 entitled "METHOD AND APPARATUS FOR PREDICTING THE RISK OF HYPOGLYCEMIA", filed Aug. 21, 2000; International Application Publication No. WO 2001/13786, Mar. 1, 2001.

What is claimed is:

1. A computer-implemented method for providing, by a glucose monitoring device of a patient, a real-time estimate of glycosylated hemoglobin (HbA1c) of said patient from a self-monitoring blood glucose (SMBG) measurement of said patient, and tracking, by said glucose monitoring device, changes in average glycemia of said patient in real-time, the method comprising the steps of:
    executing, in said glucose monitoring device, each of
        computing, by a processor of said glucose monitoring device, a surrogate fasting measurement based on SMBG data of said patient, said SMBG data being free of a fasting indication therefor;
        computing, by a processor of said glucose monitoring device, a glycation value using said surrogate fasting measurement in a predetermined glycation equation comprising a calibration offset based on a computed surrogate seven-point SMBG profile of said patient in which values of said profile are based on said SMBG data, which is free of a mealtime indication therefor;
        computing, by a processor of said glucose monitoring device, said glycation value as an initial estimate of HbA1c upon initialization of tracking of said patient's average glycemia;
        updating, by a processor of said glucose monitoring device, said glycation value by using an updated SMBG value in said predetermined glycation equation, said updated SMBG value being based on a subsequent computed surrogate fasting measurement, which is based on updated SMBG data of said patient that is free of a fasting indication therefor;
        computing, by a processor of said glucose monitoring device, an updated estimate of HbA1c using said initial estimate of HbA1c and said updated glycation value in a predetermined HbA1c estimation equation; and
        outputting, by a processor of said glucose monitoring device, said updated estimate of HbA1c to said patient,
    wherein said glucose monitoring device is configured to physically contact one or more samplings of said patient yielding (a) computing by said glucose monitoring device of said SMBG data on which said computed surrogate fasting measurement and said computed surrogate seven-point profile are based, and (b) computing by said glucose monitoring device of said updated SMBG data on which said subsequent computed surrogate fasting measurement is based, and
    wherein said samplings define said values of said computed surrogate seven-point profile, in which said values are compartmentalized by said glucose monitoring device according to predetermined timings to define calibration factors, from said values, as inputs for said calibration offset of said predetermined glycation equation.

2. The computer-implemented method of claim 1, wherein the steps of computing a surrogate fasting measurement and computing a subsequent surrogate fasting measurement respectively comprise computing an average of said SMBG data and an average of said updated SMBG data, in which each of said SMBG data and said updated SMBG data corresponds to a defined time of day over a defined range of days.

3. The computer-implemented method of claim 2, wherein the defined time of day comprises between 6:00 and 10:00.

4. The computer-implemented method of claim 2, wherein the defined range of days comprises 3 days.

5. The computer-implemented method of claim 1, further comprising the steps of:
    updating, by a processor of said glucose monitoring device, said updated estimate of HbA1c by:
        using a subsequent updated SMBG value in said predetermined glycation equation based on a further subsequent computed surrogate fasting measurement, which is based on further updated SMBG data of said patient that is free of a fasting indication therefor, to compute a further updated glycation value; and
        computing a further updated estimate of HbA1c using a last updated estimate of HbA1c and said further updated glycation value in said predetermined HbA1c estimation equation; and outputting, by a processor of said glucose monitoring device, said further updated estimate of HbA1c to said patient.

6. The computer-implemented method of claim 5, wherein said predetermined glycation equation is given by:

$$f(SMBG_i)=MAX(0.99*(4.756+0.0049*mP_0(t)+CalA1c),5)$$

where $mP_0(t)$ is the average surrogate fasting glucose over a predetermined period of time and is updated every time a new surrogate fasting glucose measurement is computed;

where CalA1c is said calibration offset;

the initial estimate of HbA1c is given by $eA1c(t_0)=f(SMBG_{t_0})$; and the updated estimate of HbA1c is given by $$eA1c(t)=0.9512*eA1c(t-1 \text{ day})+0.0488*f(SMBG_t).$$

7. The computer-implemented method of claim 6, wherein $CalA1c=0.0065*\theta_1+0.0044*\theta_2$, and wherein $\theta_1$ and $\theta_2$ are said calibration factors and are predefined for said computed surrogate seven-point SMBG profile of said patient.

8. The computer-implemented method of claim 7, wherein the surrogate seven-point SMBG profile is computed by a processor of said glucose monitoring device by using compartmental modelling to aggregate said SMBG data, said updated SMBG data, and said further updated SMBG data into predefined time bins defined for said predefined timings.

9. The computer-implemented method of claim 8, wherein the predefined time bins comprise 6:00-10:00, 10:01-13:00, 13:01-16:00, 16:01-19:00, 19:01-21:00, and 21:01-23:59.

10. The computer-implemented method of claim 9, wherein the surrogate seven-point SMBG profile is computed by:
  computing the mean of values in the 6:00-10:00 time bin to determine a pre-breakfast seven-point blood-glucose (BG) value;
  identifying the maximum value in the 10:01-13:00 time bin to determine a post-breakfast seven-point blood-glucose (BG) value;
  identifying the minimum value in the 10:01-13:00 time bin to determine a pre-lunch seven-point blood-glucose (BG) value;
  computing the mean of values in the 13:01-16:00 time bin to determine a post-lunch seven-point blood-glucose (BG) value;
  computing the mean of values in the 16:01-19:00 time bin to determine a pre-dinner seven-point blood-glucose (BG) value;
  computing the mean of values in the 19:01-21:00 time bin to determine a post-dinner seven-point blood-glucose (BG) value; and
  computing the mean of values in the 21:01-23:59 time bin to determine a bedtime seven-point blood-glucose (BG) value.

11. A system for providing, by a glucose monitoring device of a patient, a real-time estimate of glycosylated hemoglobin (HbA1c) of said patient from a self-monitoring blood glucose (SMBG) measurement of said patient, and tracking, by said glucose monitoring device, changes in average glycemia of said patient in real-time, the system comprising, in said glucose monitoring device, one or more processors, one or more computer-readable tangible storage devices, and program instructions stored on at least one of the one or more storage devices for execution by at least one of the one or more processors, the program instructions each being configured for execution in said glucose monitoring device and comprising:
  first program instructions which when executed cause at least one of the one or more processors to compute a surrogate fasting measurement based on SMBG data of said patient, said SMBG data being free of a fasting indication therefor;
  second program instructions which when executed cause at least one of the one or more processors to compute a glycation value using the said surrogate fasting measurement in a predetermined glycation equation comprising a calibration offset based on a computed surrogate seven-point SMBG profile of said patient in which values of said profile are based on said SMBG data, which is free of a mealtime indication therefor;
  third program instructions which when executed cause at least one of the one or more processors to output said glycation value as an initial estimate of HbA1c upon initialization of tracking of said patient's average glycemia;
  fourth program instructions which when executed cause at least one of the one or more processors to update said glycation value by using an updated SMBG value in said predetermined glycation equation, said updated SMBG value being based on a subsequent computed surrogate fasting measurement, which is based on updated SMBG data of said patient that is free of a fasting indication therefor;
  fifth program instructions which when executed cause at least one of the one or more processors to compute an updated estimate of HbA1c using said initial estimate of HbA1c and said updated glycation value in a predetermined HbA1c estimation equation; and
  sixth program instructions which when executed cause at least one of the one or more processors to output said updated estimate of HbA1c to said patient,
  wherein said glucose monitoring device is configured to physically contact one or more samplings of said patient yielding (a) computing by said glucose monitoring device of said SMBG data on which said computed surrogate fasting measurement and said computed surrogate seven-point profile are based, and (b) computing by said glucose monitoring device of said updated SMBG data on which said subsequent computed surrogate fasting measurement is based, and
  wherein said samplings define said values of said computed surrogate seven-point profile, in which said values are compartmentalized by said glucose monitoring device according to predetermined timings to define calibration factors, from said values, as inputs for said calibration offset of said predetermined glycation equation.

12. The system of claim 11, wherein the first program instructions and the fourth program instructions respectively compute the surrogate fasting measurement and the subsequent computed surrogate fasting measurement by computing an average of said SMBG data, as to said first program instructions, and an average of said updated SMBG data, as to said fourth program instructions, in which each of said SMBG data and said updated SMBG data corresponds to a defined time of day over a defined range of days.

13. The system of claim 12, wherein the defined time of day comprises between 6:00 and 10:00.

14. The system of claim 12, wherein the defined range of days comprises 3 days.

15. The system of claim 11, further comprising seventh program instructions which when executed cause at least one of the one or more processors to update said updated estimate of HbA1c by:
 using a subsequent updated SMBG value in said predetermined glycation equation based on a further subsequent computed surrogate fasting measurement, which is based on further updated SMBG data of said patient that is free of a fasting indication therefor, to compute a further updated glycation value; and
 computing a further updated estimate of HbA1c using a last updated estimate of HbA1c and said further updated glycation value in said predetermined HbA1c estimation equation.

16. The system of claim 15, wherein said predetermined glycation equation is given by:

$$f(SMBG_t) = MAX(0.99*(4.756+0.0049*mP_0(t)+CalA1c),5)$$

where $mP_0(t)$ is the average surrogate fasting glucose over a predetermined period of time and is updated every time a new surrogate fasting glucose measurement is computed;
where CalA1c is said calibration offset;
the initial estimate of HbA1c is given by $eA1c(t_0) = f(SMBG_{t_0})$; and
the updated estimate of HbA1c is given by $$eA1c(t) = 0.9512*eA1c(t-1\ day) + 0.0488*f(SMBG_t).$$

17. The system of claim 16, wherein CalA1c=$0.0065*\theta_1+0.0044*\theta_2$, and wherein $\theta_1$ and $\theta_2$ are said calibration factors and are predefined for said computed surrogate seven-point SMBG profile of said patient.

18. The system of claim 17, further comprising eighth program instructions which when executed cause at least one of the one or more processors to compute the surrogate seven-point SMBG profile by using compartmental modelling to aggregate said SMBG data, said updated SMBG data, and said further updated SMBG data into predefined time bins defined for said predefined timings.

19. The system of claim 18, wherein the predefined time bins comprise 6:00-10:00, 10:01-13:00, 13:01-16:00, 16:01-19:00, 19:01-21:00, and 21:01-23:59.

20. The system of claim 19, wherein the surrogate seven-point SMBG profile is computed by:
 computing the mean of values in the 6:00-10:00 time bin to determine a pre-breakfast seven-point blood-glucose (BG) value;
 identifying the maximum value in the 10:01-13:00 time bin to determine a post-breakfast seven-point blood-glucose (BG) value;
 identifying the minimum value in the 10:01-13:00 time bin to determine a pre-lunch seven-point blood-glucose (BG) value;
 computing the mean of values in the 13:01-16:00 time bin to determine a post-lunch seven-point blood-glucose (BG) value;
 computing the mean of values in the 16:01-19:00 time bin to determine a pre-dinner seven-point blood-glucose (BG) value;
 computing the mean of values in the 19:01-21:00 time bin to determine a post-dinner seven-point blood-glucose (BG) value; and
 computing the mean of values in the 21:01-23:59 time bin to determine a bedtime seven-point blood-glucose (BG) value.

21. A non-transient computer-readable medium having stored therein computer-executable instructions for providing, by a glucose monitoring device of a patient, a real-time estimate of glycosylated hemoglobin (HbA1c) of said patient from a self-monitoring blood glucose (SMBG) measurement of said patient, and tracking, by said glucose monitoring device, changes in average glycemia of said patient in real-time, said instructions each being configured for execution in said glucose monitoring device and comprising:
 first program instructions which when executed cause at least one processor of said glucose monitoring device to compute a surrogate fasting measurement based on SMBG data of said patient, said SMBG data being free of a fasting indication therefor;
 second program instructions which when executed cause at least one processor of said glucose monitoring device to compute a glycation value using the said surrogate fasting measurement in a predetermined glycation equation comprising a calibration offset based on a computed surrogate seven-point SMBG profile of said patient in which values of said profile are based on said SMBG data, which is free of a mealtime indication therefor;
 third program instructions which when executed cause at least one processor of said glucose monitoring device to output said glycation value as an initial estimate of HbA1c upon initialization of tracking of said patient's average glycemia;
 fourth program instructions which when executed cause at least one processor of said glucose monitoring device to update said glycation value by using an updated SMBG value in said predetermined glycation equation, said updated SMBG value being based on a subsequent computed surrogate fasting measurement, which is based on updated SMBG data of said patient;
 fifth program instructions which when executed cause at least one processor of said glucose monitoring device to compute an updated estimate of HbA1c using said initial estimate of HbA1c and said updated glycation value in a predetermined HbA1c estimation equation; and
 sixth program instructions which when executed cause at least one processor of said glucose monitoring device to output said updated estimate of HbA1c to said patient,
 wherein said glucose monitoring device is configured to physically contact one or more samplings of said patient yielding (a) computing by said glucose monitoring device of said SMBG data on which said computed surrogate fasting measurement and said computed surrogate seven-point profile are based, and (b) computing by said glucose monitoring device of said updated SMBG data on which said subsequent computed surrogate fasting measurement is based, and
 wherein said samplings define said values of said computed surrogate seven-point profile, in which said values are compartmentalized by said glucose monitoring device according to predetermined timings to define calibration factors, from said values, as inputs for said calibration offset of said predetermined glycation equation.

22. The non-transient computer-readable medium of claim 21, wherein the surrogate fasting measurement and the subsequent surrogate fasting measurement are computed by, respectively, computing an average of said SMBG data and an average of said updated SMBG data, in which each of said SMBG data and said updated SMBG data corresponds to a defined time of day over a defined range of days.

23. The non-transient computer-readable medium of claim 22, wherein the defined time of day comprises between 6:00 and 10:00.

24. The non-transient computer-readable medium of claim 22, wherein the defined range of days comprises 3 days.

25. The non-transient computer-readable medium of claim 21, further comprising seventh program instructions which when executed cause at least one processor of said glucose monitoring device to update said updated estimate of HbA1c by:
using a subsequent updated SMBG value in said predetermined glycation equation based on a further subsequent computed surrogate fasting measurement, which is based on further updated SMBG data of said patient, to compute a further updated glycation value; and
computing a further updated estimate of HbA1c using a last updated estimate of HbA1c and said further updated glycation value in said predetermined HbA1c estimation equation.

26. The non-transient computer-readable medium of claim 25,
wherein said predetermined glycation equation is given by:

$$f(SMBG_t) = MAX(0.99*(4.756+0.0049*mP_0(t)+CalA1c),5)$$

where $mP_0(t)$ is the average surrogate fasting glucose over a predetermined period of time and is updated every time a new surrogate fasting glucose measurement is computed;
where CalA1c is said calibration offset;
the initial estimate of HbA1c is given by $eA1c(t_0)=f(SMBG_{t_0})$; and
the updated estimate of HbA1c is given by $$eA1c(t) = 0.9512*eA1c(t-1\ day)+0.0488*f(SMBG_t).$$

27. The non-transient computer-readable medium of claim 26, wherein $CalA1c = 0.0065*\theta_1 + 0.0044*\theta_2$, and wherein $\theta_1$ and $\theta_2$ are said calibration factors and are predefined for said computed surrogate seven-point SMBG profile of said patient.

28. The non-transient computer-readable medium of claim 27, further comprising eighth program instructions which when executed cause at least one processor of said glucose monitoring device to compute the surrogate seven-point SMBG profile by using compartmental modelling to aggregate said SMBG data, said updated SMBG data, and said further updated SMBG data into predefined time bins defined for said predefined timings.

29. The non-transient computer-readable medium of claim 28, wherein the predefined time bins comprise 6:00-10:00, 10:01-13:00, 13:01-16:00, 16:01-19:00, 19:01-21:00, and 21:01-23:59.

30. The non-transient computer-readable medium of claim 29,
wherein the surrogate seven-point SMBG profile is computed by:
computing the mean of values in the 6:00-10:00 time bin to determine a pre-breakfast seven-point blood-glucose (BG) value;
identifying the maximum value in the 10:01-13:00 time bin to determine a post-breakfast seven-point blood-glucose (BG) value;
identifying the minimum value in the 10:01-13:00 time bin to determine a pre-lunch seven-point blood-glucose (BG) value;
computing the mean of values in the 13:01-16:00 time bin to determine a post-lunch seven-point blood-glucose (BG) value;
computing the mean of values in the 16:01-19:00 time bin to determine a pre-dinner seven-point blood-glucose (BG) value;
computing the mean of values in the 19:01-21:00 time bin to determine a post-dinner seven-point blood-glucose (BG) value; and
computing the mean of values in the 21:01-23:59 time bin to determine a bedtime seven-point blood-glucose (BG) value.

* * * * *